US010287228B2

(12) United States Patent
Da Costa Leão et al.

(10) Patent No.: US 10,287,228 B2
(45) Date of Patent: May 14, 2019

(54) ANTIMALARIAL AGENT, METHODS AND USES THEREOF

(71) Applicants: UNIVERSIDADE DO PORTO, Oporto (PT); INSTITUTO DE HIGIENE E MEDICINA TROPICAL, Lisbon (PT); INSTITUTO POLITÉCNICO DO PORTO, Oporto (PT)

(72) Inventors: Pedro Nuno Da Costa Leão, Oporto (PT); Maria Do Rosário Martins, Oporto (PT); Margarida Costa, Oporto (PT); Vítor Vasconcelos, Oporto (PT); Valentina Domingues, Oporto (PT); Fátima Nogueira, Lisbon (PT)

(73) Assignees: UNIVERSIDADE DO PORTO, Oporto (PT); INSTITUTO DE HIGIENE E MEDICINA TROPICAL, Lisbon (PT); INSTITUTO POLITÉCNICO DO PORTO, Oporto (PT); CIIMAR—Terminal de Cruzeiros do Porto de Leixões, Matosinhos (PT)

( * ) Notice: Subject to any disclaimer, the term of this patent is extended or adjusted under 35 U.S.C. 154(b) by 0 days.

(21) Appl. No.: 15/739,880

(22) PCT Filed: Jun. 27, 2016

(86) PCT No.: PCT/IB2016/053823
§ 371 (c)(1),
(2) Date: Dec. 26, 2017

(87) PCT Pub. No.: WO2016/207869
PCT Pub. Date: Dec. 29, 2016

(65) Prior Publication Data
US 2018/0186713 A1 Jul. 5, 2018

(30) Foreign Application Priority Data

Jun. 25, 2015 (PT) .................................... 108584

(51) Int. Cl.
*C07C 43/23* (2006.01)
*C12P 7/22* (2006.01)
*C12R 1/01* (2006.01)
*A61P 33/06* (2006.01)

(52) U.S. Cl.
CPC ............. *C07C 43/23* (2013.01); *A61P 33/06* (2018.01); *C12P 7/22* (2013.01); *C12R 1/01* (2013.01)

(58) Field of Classification Search
CPC . C07C 43/23; A61P 33/06; C12P 7/22; C12R 1/01
USPC ......................................................... 514/718
See application file for complete search history.

(56) References Cited

FOREIGN PATENT DOCUMENTS

EP 2177496 A1 4/2010

OTHER PUBLICATIONS

Dean et al. Journal of the Chemical Society (1955) 11-17.*
Akhlaghinia et al. "A mild and simple iodination of phenols with trichloroisocyanuric acid/I2/Wet SiO2 system." Journal of the Brazilian Chemical Society 21.1 (2010): 3-6.
Baek. "Halogenation of Resorcinol Derivatives." Bulletin of the Korean Chemical Society 9.1 (1988): 13-15.
Dean et al. "The chemistry of fungi. Part XXIV. The formation of diquinones." Journal of the Chemical Society (1955): 11-17.
González et al. "Synthesis of hierridin, a phenol from the lichen, Ramalina hierrensis." Phytochemistry 31.4 (1992): 1436-1439.
Leão et al. "Antitumor activity of hierridin B, a cyanobacterial secondary metabolite found in both filamentous and unicellular marine strains." PloS one 8.7 (2013): e69562. 8 pages.
Mendonça et al. "Trichloroisocyanuric acid in 98% sulfuric acid: A superelectrophilic medium for chlorination of deactivated arenes." Applied Catalysis A: General 401.1 (2011): 176-181.
Nakamura et al. "Cylindrocyclophane biosynthesis involves functionalization of an unactivated carbon center." Journal of the American Chemical Society 134.45 (2012): 18518-18521.
Papendorf et al. "Hierridin B and 2, 4-dimethoxy-6-heptadecylphenol, secondary metabolites from the cyanobacterium Phormidium ectocarpi with antiplasmodial activity." Phytochemistry 49.8 (1998): 2383-2386.

* cited by examiner

*Primary Examiner* — Kahsay Habte
(74) *Attorney, Agent, or Firm* — Leason Ellis LLP (57) ABSTRACT

The present disclosure relates to compounds and compositions for the treatment of malarian diseases. The compounds comprise a class of halogenated alkyl-aromatic secondary metabolites, including hierridic C, or pharmaceutically acceptable salts, esters, solvates or prodrugs thereof. The compounds comprise a halogen; $C_1$-$C_6$ alkyl, H, COCH3, COH, CO-alkyl, or CO-aryl; and a $C_3$-$C_{30}$ alkyl. In at least one embodiment, the compound is 3-chloro-4,6-dimethoxy-2-pentadecylphenol. The present disclosure also relates to methods of obtain the compounds from a solution comprising a cyanobacterium.

8 Claims, 6 Drawing Sheets

ANTIMALARIAL AGENT, METHODS AND USES THEREOF

CROSS REFERENCE TO RELATED APPLICATIONS

This application is a U.S. National Stage Application under 35 U.S.C. § 371 of International Patent Application No. PCT/IB2016/053823, filed Jun. 27, 2016, which claims priority to Portugal Application No. 108584, filed Jun. 25, 2015, both of which are hereby incorporated by reference in their respective entireties.

TECHNICAL FIELD

The present disclosure relates to a compound or a pharmaceutically acceptable salt, ester, solvate or prodrug thereof, for use in medicine, in particular as antimalarial agent.

The present solution relates to halogenated alkyl-aromatic secondary metabolites, and their application as an antimalarial agent.

Furthermore, the present disclosure also relates to methods to obtain antimalarial agents and compounds, and chemically synthesize such compounds under laboratory conditions.

TECHNICAL BACKGROUND

Malaria is present in more than one hundred countries and according to the World Health Organization, there were an estimated 198 million cases of malaria worldwide (range 124-283 million) in 2013, and an estimated 584 000 deaths (range 367 000-755 000). 90% of all malaria deaths occur in Africa.

Malaria is caused by *Plasmodium* parasites. These parasites are spread to people through the bites of infected *Anopheles* mosquitoes, called "malaria vectors", which bite mainly between dusk and dawn. There are four protozoa parasite species that cause malaria in humans: *Plasmodium* (*P.*) *falciparum*; *P. vivax*; *P. malariae* and *P. ovale*. The parasites *P. falciparum* and *P. vivax* are the most common. Death by malaria is almost exclusively caused by *P. falciparum*.

Most of the drugs currently used for treating malaria patients include chloriquine, atovaquone-proguanil (Malarone®), artemether-lumefantrine (Coartem®), mefloquine (Lariam®), quinine, quinidine, doxycycline (used in combination with quinine), clindamycin (used in combination with quinine), artesunate.

Presently, there is a growing need for antimalarial agents, either for monotherapy or as multi-drug therapies as drug-resistant strains are emerging worldwide, in particular mefloquine and chloroquine resistant strains. Therefore, new agents able to kill the resistant malaria parasites are warranted.

These facts are disclosed in order to illustrate the technical problem addressed by the present disclosure.

General Description

The solution now disclosed relates to antimalarial agents and to methods to obtain them. The advantage of the present disclosure is that there is no strain of *P. falciparum* known to be resistant to halogenated alkyl-aromatic secondary metabolite, in particular hierridin C and its derivatives. This advantage is relevant as death by malaria is almost exclusively caused by *P. falciparum*.

The present disclosure relates to an antimalarial agent, in particular hierridin C, a halogenated alkyl-aromatic secondary metabolite, obtainable from the cyanobacterium *Cyanobium* sp. LEGE 06113, in particular the cyanobacterium *Cyanobium* sp. LEGE 06113 which was received on 29 May 2015 and accepted for deposit for patent purposes on 15 Jun. 2015 at the Scottish Association for Marine Science Culture Collection of Algae and Protozoa (CCAP), Oban, Argyll PA37 1QA, Scotland, United Kingdom—International Depositary Authority under the Budapest Treaty—under the CCAP number 1436/1.

Furthermore, the solution herein presented relates to processes used to obtain this compound from the cyanobacterium culture; furthermore it also relates to compounds sharing the same halogenated skeleton as hierridin C, and to its use in formulations for treating, preventing or inhibiting malaria in humans.

The hierridin C is a new antimalarial agent, which can be used to treat malaria, one of the most prevalent and life threatening infectious diseases in the developing world. It is a natural product and can be obtained from a renewable, photoautotrophic source by mass culturing in the laboratory or open ponds or alternatively it may be chemically synthetized.

Cyanobacteria are a large and widely spread group of photoautotrophic prokaryotes with a noteworthy ecological relevance being the only prokaryotes capable to carry out oxygenic photosynthesis, in which light energy is converted into chemical energy.

Cyanobacterial secondary metabolites represent a vast diversity of structures and have been isolated from a number of cyanobacterial genera, in particular cyanobacterial secondary metabolites have been mainly isolated from filamentous forms of the Oscillatoriales and Nostocales orders. Picocyanobacteria from the chroococcalean genera *Cyanobium*, *Prochlorococcus* and *Synechococcus* currently constitute the source of a very small fraction (less than 1%) of the reported cyanobacterial secondary metabolites. These cyanobacterial secondary metabolites may have potential therapeutic use.

Based on the International Union of Pure and Applied Chemistry (IUPAC) definitions, an alkyl group is defined as a univalent group derived from alkanes by removal of a hydrogen atom from any carbon atom —$C_nH_{2n+1}$. The groups derived by removal of a hydrogen atom from a terminal carbon atom of unbranched alkanes form a subclass of normal alkyl (n-alkyl) groups $H(CH_2)_n$. The groups $RCH_2$, $R_2CH(R \neq H)$, and $R_3C(R \neq H)$ are primary, secondary and tertiary alkyl groups, respectively. An aryl group is derived from arenes (monocyclic and polycyclic aromatic hydrocarbons) by removal of a hydrogen atom from a ring carbon atom.

"Alkyl" includes "lower alkyl" and extends to cover carbon fragments having up to 30 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, 2-(cyclododecyl)ethyl, adamantyl, and the like.

"Lower alkyl" means alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

Halogen is an element selected from the list consisting of: F, Cl, Br, I, At.

The half maximal inhibitory concentration (IC$_{50}$) value indicates the concentration of a particular drug or other substance (inhibitor) necessary to inhibit a specific biological, biochemical or biological function or process (or component of a process, i.e. an enzyme, cell, cell receptor or microorganism) function by half.

Antimalarial activity can be defined as the capability of compounds to inhibit the growth/viability of parasites. The half maximal inhibitory concentration (IC50) value for an antimarial drug indicates the concentration necessary to inhibit 50% of the parasites. The IC$_{50s}$ of hierridin C against the two parasite strains 3D7 (sensitive to chloroquine) and Dd2 (resistant to chloroquine and mefloquine) was in the low M range, which is identical to that of primaquine (an antimalarial in use despite its toxicity). Resistance indices (RI) of approximately 1 (RI=0.93) indicate that hierridin C kill the parasites via a different mechanism from chloroquine and mefloquine.

Hierridin B is a cyanobacterial secondary metabolite and the isolation of hierridin B from one of such strains, *Cyanobium* sp. LEGE 06113 was reported (Leão, P. N. et al. (2013) Antitumor Activity of Hierridin B, a Cyanobacterial Secondary Metabolite Found in both Filamentous and Unicellular Marine Strains. *PloS ONE* 8, doi:10.1371/journal.pone.0069562). This alkyl-aromatic metabolite had been previously isolated from a filamentous cyanobacterium, together with an extended chain analogue (Papendorf, O., König, G. M. & Wright, A. D. (1998) Hierridin B and 2,4-dimethoxy-6-heptadecyl-phenol, secondary metabolites from the cyanobacterium *Phormidium ectocarpi* with antiplasmodial activity. *Phytochemistry* 49, 2383-2386).

The polyhydroxylated aromatic moiety in hierridin B is hypothesized to originate from the action of a type III PKS, along the lines of the logic put forward for the cylindrocyclophanes (Nakamura, H. et al, 2012, Cylindrocyclophane biosynthesis involves functionalization of an unactivated carbon center. *J Am Chem Soc* 134(45):18518-21). Compound hierridin B showed modest, selective cytotoxicity towards HT-29 colon adenocarcinoma human cells (Leão, P. N. et al. (2013) Antitumor Activity of Hierridin B, a Cyanobacterial Secondary Metabolite Found in both Filamentous and Unicellular Marine Strains. *PloS ONE* 8, doi: 10.1371/journal.pone.0069562).

An antiplasmodial activity was observed for a mixture of hierridin B and an extended-chain analogue (Papendorf, O., König, G. M. & Wright, A. D. (1998) Hierridin B and 2,4-dimethoxy-6-heptadecyl-phenol, secondary metabolites from the cyanobacterium *Phormidium ectocarpi* with antiplasmodial activity *Phytochemistry* 49, 2383-2386).

The low recovery (0.06%) of this metabolite (hierridin B) from the biomass of *Cyanobium* sp. LEGE 06113 hindered further evaluation of its bioactivity profile, and strongly motivated a re-isolation effort. While performing this task, another secondary metabolite was isolated from this cyanobacterium, hierridin C, which is a halogenated alkyl-aromatic secondary metabolite, in particular a chloro alkyl-aromatic secondary metabolite.

The present disclosure describes a new antimalarial agent isolated from laboratory cultures of the cyanobacterium *Cyanobium* sp. LEGE 06113, which has antimalarial activity against the strains of *P. falciparum* 3D7 and Dd2 (multidrug-resistant strain).

Figure 5:
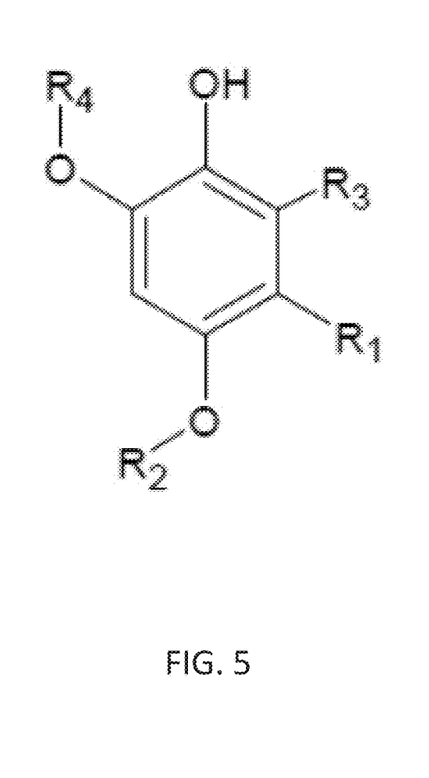
FIG. 5: Chemical structure of the alkyl-aromatic metabolite.

The present disclosure describes a compound of the formula I:

wherein:
  $R_1$ is a halogen;
  $R_2$, $R_4$ are independently selected from a group consisting of $C_1$-$C_6$ alkyl, H, COCH$_3$, COH, CO-alkyl, CO-aryl;
  $R_3$ is a $C_3$-$C_{30}$ alkyl;
  or a pharmaceutically acceptable salt, ester, solvate or prodrug thereof, for use in medicine (see FIG. 5).

In an embodiment, the compounds previously described may comprise an $R_3$ wherein the $R_3$ is a $C_{10}$-$C_{30}$ alkyl.

In an embodiment, the compounds previously described may comprise $R_1$, $R_2$, $R_3$ and $R_4$ wherein
  $R_1$ may be selected from the group consisting of F, Cl, Br;
  $R_2$, $R_4$ may be independently selected from a group consisting of $C_1$-$C_6$ alkyl;
  $R_3$ may be a $C_{15}$-$C_{21}$ alkyl.

In an embodiment, $R_2$ and $R_4$ may be equal.

Figure 4:
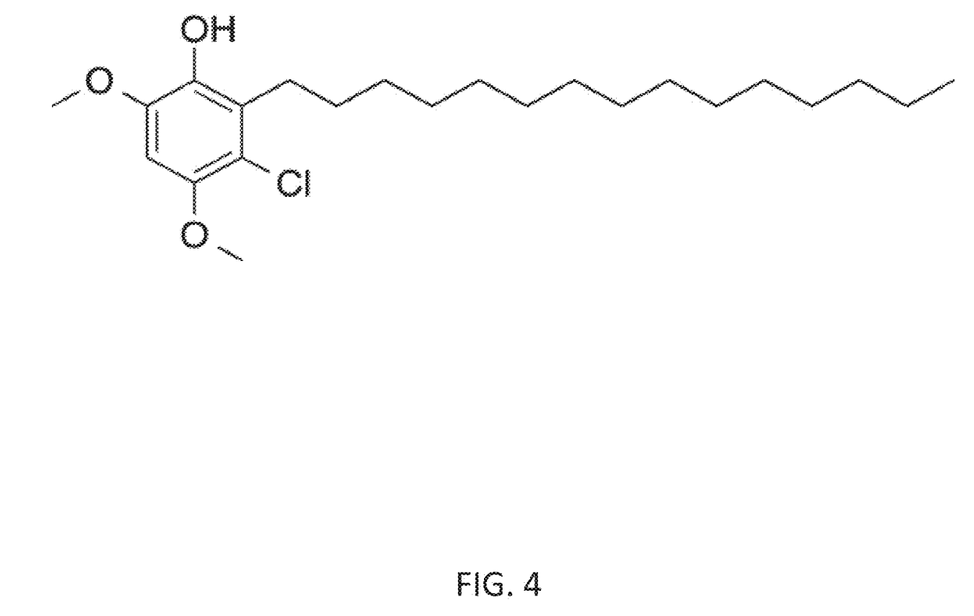
FIG. 4: Chemical structure of hierridin C.

In an embodiment, the compound may be 3-chloro-4,6-dimethoxy-2-pentadecylphenol (see FIG. 4).

In an embodiment, the compounds previously described may be used for the treatment of malarian diseases.

The present disclosure also relates to a pharmaceutical composition comprising a compound as previously defined in any of the previous embodiments and a pharmaceutically acceptable carrier, adjuvant, excipient or mixtures thereof.

The present disclosure also relates to a pharmaceutical composition wherein it is administrated via topical, oral or parental or injectable.

The present disclosure also relates to a vaccine comprising a compound as previously described in any of the embodiments.

The present disclosure also relates to a process for obtaining compound 3-chloro-4,6-dimethoxy-2-pentadecylphenol comprising in the isolation of said compound from a solution comprising a cyanobacterium, in particular the cyanobacterium *Cyanobium* sp. LEGE 06113, which was received on 29 May 2015 and accepted for deposit for patent purposes on 15 Jun. 2015 at the Scottish Association for Marine Science Culture Collection of Algae and Protozoa (CCAP)—International Depositary Authority under the Budapest Treaty—under the CCAP number 1436/1.

The compound of formula I and its derivates, in particular, hierridin C and its derivates may also be used for the treatment of antimicrobian infections, namely as antimicrobial agent, in particular for the treatment or prevention of malarian diseases.

The compound/compositions can be combined with other excipients or active substances used in the context of veterinarian or human medicine.

The compound or compositions of the present disclosure can be administered by various routes, including topical, enteral and parenteral. Parenteral administration routes include intra-arterial, intra-articular, intracavitary, intradermal, intralympathic, intramuscular, intrasynovial, intravenous, or subcutaneous. Enteral routes include oral and gastro-intestinal. Topical routes include application into the skin and mucous membranes.

In a preferred embodiment, the composition is delivered to a patient by oral administration, which can be repeated according to a clinical prescription regime.

Dosage of the composition can be adapted to the administration route, as well as to the patient profile, including age, gender, condition, disease progression, or any other phenotypic or environmental parameters.

The composition may be in a solid form such as an amorphous, crystalline or semi-crystalline powder, granules, flakes, pills, capsules and suppositories. Such a solid form can be converted into a liquid form by mixing the solid with a physiologically appropriate liquid such as solvents, solutions, suspensions and emulsions.

In another aspect, the present invention provides a method of treating a patient with a microorganism infection disease, the method comprising administering an effective amount of compound or composition of the present disclosure to the patient.

In a further aspect, the present invention provides the compound or composition of the present disclosure for use in the treatment of microorganism infections, in particular malarian disease.

Further, the present invention provides the use of compound or composition of the present disclosure in the manufacture of a medicament for the treatment of microorganism infections, namely malaria disease.

In a particular aspect, the invention provides the composition described above for use in therapy. Further, the present invention provides the composition described above for use in the treatment/prevention of microorganism infections, namely malaria disease.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

BRIEF DESCRIPTION OF THE DRAWINGS

The following figures provide preferred embodiments for the present disclosure and should not be seen as limiting the scope of the disclosure.

DETAILED DESCRIPTION

The present disclosure relates to compound of the formula I; or a pharmaceutically acceptable salt, ester, solvate or prodrug thereof, for use in medicine, in particular as antimalarial agent.

The present solution describes a new halogenated antimalarial agent, hierridin C, isolated from laboratory cultures of the cyanobacterium *Cyanobium* sp. LEGE 06113, which was received on 29 May 2015 and accepted for deposit for patent purposes on 15 Jun. 2015 at the Scottish Association for Marine Science Culture Collection of Algae and Protozoa (CCAP), Oban, Argyll PA37 1QA, Scotland, United Kingdom—International Depositary Authority under the Budapest Treaty—under the CCAP number 1436/1, which has antimalarial activity in both malaria resistant and non-resistant (multidrug-resistant Dd2 strain and 3D7 strain) strains of *P. falciparum*. The present solution also relates to a method to isolate and purify hierridin C as well as a method to synthetize hierridin C and its derivatives.

The cyanobacterium *Cyanobium* sp. LEGE 06113, isolated from a rocky beach in Portugal, was obtained from the LEGE culture collection (CIIMAR, University of Porto). The strain was cultured in multiple 6 L flasks, each with 4 L of Z8 medium supplemented with 20 g $L^{-1}$ NaCl, under constant sterile aeration and a light (photon irradiance of approximately 30 µmol $m^{-2}$ $s^{-1}$)/dark cycle of 14:10 h. The temperature was maintained at 26° C. Following a period of 1.5-2 months of growth, the cyanobacterial cells were harvested by centrifugation and rinsed with deionized water. The cyanobacterial biomass was then freeze-dried and kept at −20° C. until the extraction of hierridin C compound.

The Z8 medium used to grow the cyanobacterium *Cyanobium* sp. LEGE 06113 is prepared as it is described in Leão, P. N. et al. Antitumor Activity of Hierridin B, a Cyanobacterial Secondary Metabolite Found in both Filamentous and Unicellular Marine Strains. *PloS ONE* 8, doi:10.1371/journal.pone.0069562 (2013).

In an embodiment, the extraction and isolation of hierridin C from *Cyanobium* sp. LEGE 06113 was performed as follows: the freeze-dried cells from *Cyanobium* sp. LEGE 06113 (16.0 g, dry weight) were extracted repeatedly with a warm (<40° C.) mixture of $CH_2Cl_2$:MeOH (2:1). The resulting slurry was filtered through Whatman grade 1 qualitative filter paper (GE Healthcare Life Sciences, Little Chalfont, UK) and concentrated in a rotary evaporator to yield 2.58 g of crude extract. The crude extract was fractionated by Vacuum Liquid Chromatography (VLC) using silica gel 60 (0.015-0.040 mm, Merck KGaA, Damstadt, Germany) as stationary phase.

In an embodiment, four fractions (A, A1, A2 and A3) were initially collected using 9:1, 87:13, 17:3 and 41:9 mixtures of n-hexane:EtOAc, respectively, as mobile phase. A steeper mobile-phase gradient was then applied to the column, from 4:1 n-hexane:EtOAc to 100% EtOAc and then to 100% MeOH, resulting in eight additional fractions.

The $^1$H NMR ($CDCl_3$, 400 MHz) inspection of the VLC fractions suggested the presence of hierridin B in fraction A1 (20.4 mg). This fraction was further separated by semi-preparative RP-HPLC with a Luna C18 column (10 µm, 250×10 mm, Phenomenex) under isocratic conditions (97% aqueous MeCN, 3 mL $min^{-1}$). A chromatographic peak eluting with a retention time of 27.1 min was collected and found to contain hierridin B as a major constituent, by $^1$H NMR analysis ($CDCl_3$, 400 MHz). The sample was re-injected into the HPLC system fitted with the above mentioned column, and further fractionated, using 90% MeCN (aq) as the isocratic mobile phase. Pure hierridin B (0.4 mg) eluted at 41.2 min and an additional peak eluting at 50.7 min was collected. The $^1$H NMR ($CDCl_3$, 400 MHz) of this latter peak showed a major constituent with a set of resonances that indicated relatedness to compound hierridin B. An additional round of analytical-scale HPLC with a Synergi Fusion-RP column (4 μm, 250×4.6 mm, Phenomenex) and using isocratic elution with 85% MeCN (aq), afforded hierridin C (RT=38.9 min) as a white amorphous solid (0.3 mg).

In an embodiment, the structural elucidation of hierridin C was performed. The $^1$H NMR spectrum of hierridin C in CDCl$_3$ bears resemblance to that of hierridin B (Leão, P. N. et al. Antitumor Activity of Hierridin B, a Cyanobacterial Secondary Metabolite Found in both Filamentous and Unicellular Marine Strains. PloS ONE 8, doi:10.1371/journal.pone.0069562 (2013)). Still, a single aromatic proton resonance is observed for hierridin C, suggesting a penta-substituted aryl moiety. A combination of 1D (1H, 13C) and 2D (HSQC, HMBC, COSY) NMR data for hierridin C in DMSO-d revealed the architecture of the aromatic moiety as a 2,3,4,6-substituted phenol with an aliphatic chain as one of the substituents. A $^1$H NMR spectrum of hierridin C in DMSO-d$_6$ displayed one exchangeable OH peak (bs δ8.30); the aromatic proton resonated as a singlet at δ6.66 and highly diagnostic sharp singlets for two aromatic methoxy groups were observed further upfield at δ3.81 and δ3.77. A characteristic signal for a benzylic methylene resonated at δ2.66 (t, J=7.6 Hz) and one methylene signal was also distinguishable at δ1.42 (m). The data were completed by a CH$_2$ envelope (δ1.29-δ1.23) and by a methyl triplet at δ0.85 (J=7.0 Hz).

Figure 1A:
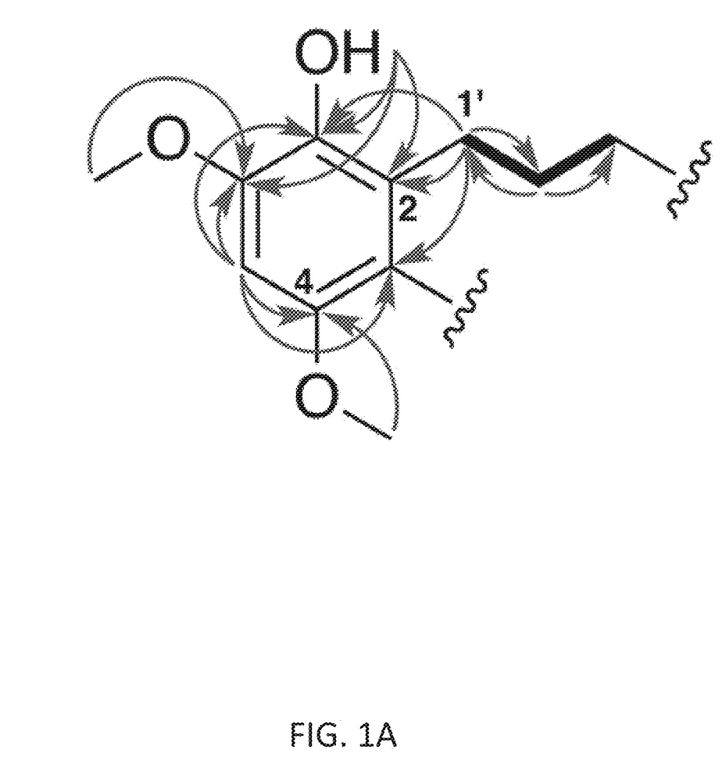
FIGS. 1A-B: HMBC and COSY correlations establishing the partial structures of the aromatic moiety (FIG. 1A) and aliphatic chain terminus (FIG. 1B) of hierridin B.
Figure 1B:
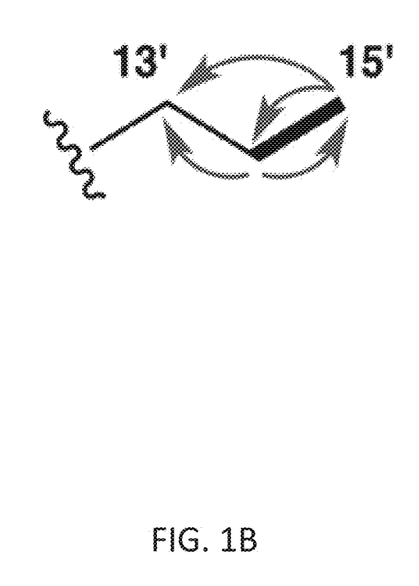

In an embodiment, the $^{13}$C spectrum for hierridin C in the same solvent (DMSO-d) showed six downfield resonances (δ147.6; δ146.3; δ138.3; δ128.0; δ112.8; δ96.6), the two methoxy carbon signals at δ56.6 and δ56.1 and a methylene resonance at δ31.3. Other methylene signals were observed in the range δ29.0-28.7, as well as at δ28.2, 27.0, and 22.1. Finally, a methyl carbon peak was observed at δ13.9. The analysis of the combined 1D and 2D NMR data for hierridin C allowed establishing two partial structures (FIGS. 1A-B). The elucidation of the structure of the aromatic "head" of the molecule (FIG. 1A) was facilitated by HMBC correlations from the aromatic proton (δ6.66, H-5) to four downfield carbons at δ147.6, δ146.3, δ138.3 and δ112.8 (C-4, C-6, C-1 and C-3, respectively), suggesting that the carbon resonating at δ128.0 (C-2) should be para to H-5. The benzylic protons (δ2.66, H$_2$-1') resonance showed correlations to three aromatic carbons at δ138.3, δ128.0 and δ112.8 (C-1, C-2 and C-3, respectively). This allowed assigning the carbons resonating at δ147.6 (C-6) and δ146.3 (C-4) as ortho to H-5. In addition, each of these carbons was found to be O-methylated, on the basis of HMBC correlations from the methoxy protons at δ3.81 (H$_3$-8) and δ3.77 (H$_3$-7) to C-6 and C-4, respectively. The final substituent arrangement was established from HMBC correlations between the exchangeable phenol proton (OH-1) and three carbons at δ146.3, δ138.3 and δ128.0 (C-6, C-1 and C-2, respectively), leading to the assignment of the hydroxyl group to the carbon at δ138.3 (C-1) and of its position as adjacent to both C-6 and C-2. This and the previously assumed constraints resulted in the allocation of the alkyl substituent to the carbon at δ128.0 (C-2) and subsequent assignment of the carbons at δ112.8 (C-3) and δ147.6 (C-4) as ortho and meta to C-2. The identity of the heteroatom substituent at C-3 was not clear at this time. The partial structure was finalized by the straightforward assignment, on the basis of COSY and HMBC correlations, of the methylene protons resonating at δ1.42 (H$_2$-2') as being in an intermediate position between the benzylic methylene and the CH$_2$ envelope. A second partial structure (FIG. 1B) was extracted from the NMR data and corresponded to the terminus of an aliphatic chain. HMBC correlations were observed from the terminal methyl group, resonating at δ0.85 (H$_3$-15'), to two aliphatic carbons at δ31.3 (C-13') and δ22.1 (C-14'). A COSY correlation was also observed between H$_3$-15' and methylene protons at 1.24 (H$_2$-14'), which in turn showed HMBC correlations to carbons at δ31.3 and δ13.9 (C-13' and C-15', respectively), thus establishing a three-carbon sequence. The protons at position 13' resonated at δ1.23 and were HMBC-correlated to the CH$_2$ envelope, thus finalizing the partial structure.

Figure 2:
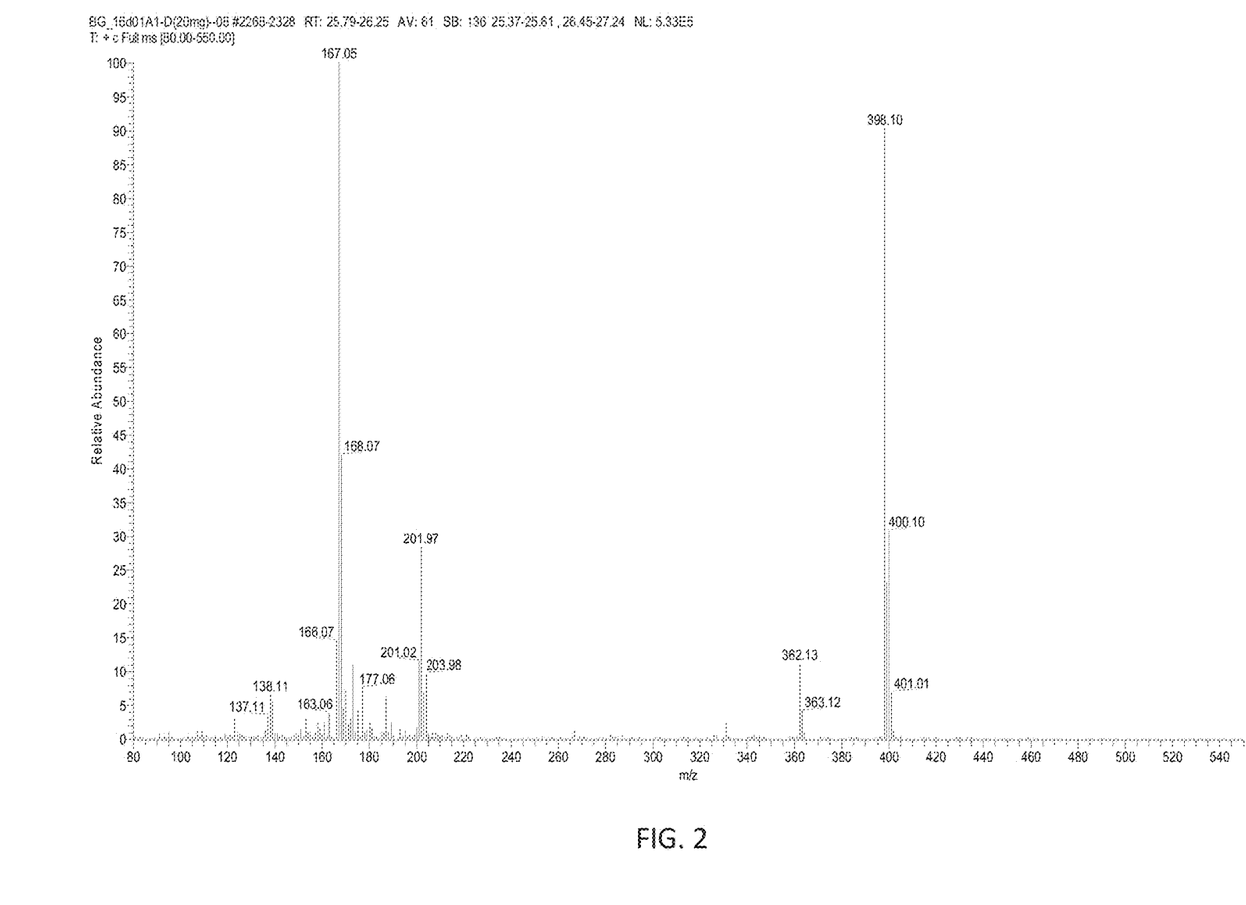
FIG. 2: GC-MS analysis of hierridin C. Electron ionization (EI) mass spectrum of; Expanded clusters at m/z 398 (molecular ion cluster) and m/z 201 (aromatic moiety after fragmentation at the benzylic position).

In an embodiment, from the NMR data, the substituent at C-3 was unknown and the precise number of CH$_2$ groups in the aliphatic chain difficult to estimate through the integration of the $^1$H NMR data of hierridin C. Gas chromatography-mass spectrometry (GC-MS) analysis of hierridin C provided enough information to fully elucidate the structure. The MS spectrum of hierridin C (FIG. 2) exhibited a molecular ion cluster with a monoisotopic m/z 398 and an isotope pattern highly consistent with the presence of one chlorine atom (calcd. m/z 399 x %; m/z 400 x %; m/z 401 x %; obs. 399 x %; m/z 400 x %; m/z 401 x %), thus assigned as the substituent at C-3. This was corroborated by the observation of the same isotope pattern for the aromatic "head" following benzylic fragmentation (monoisotopic m/z of 201, C$_9$H$_{10}$ClO$_3^+$). A C$_{15}$ saturated chain was thus revealed, further substantiating the relatedness of hierridin B and hierridin C, which therefore feature a similar aliphatic moiety. It was further possible to ionize the compound by direct injection into an Orbitrap (Thermo, USA) ionization chamber and obtain the accurate mass confirming the molecular formula for hierridin C.

In an embodiment, the chemical synthesis of hierridin C is also disclosed. Hierridin C may be synthetized following the methodology already stablished for the synthesis of a hierridin from Ramalina hierrensis (Gonzalez, A. G.; Barrera, J. B.; Perez, E. M. R. (1992) Phytochemistry 31, 4, 1436-1439). The substitution of an H of the aromatic ring by a halogen may be performed as described in Mendonca, G. F; Senra, M. R.; Esteves, P. M.; Mattos, M. C. S. (2011) Applied Catalysis A: General 401, 176-181; Akhlaghinia, B. and Rahmani, M. (2010) J Braz. Chem. Soc., Vol 21(1) pages 3-6 and/or any of the methodologies described in Baek, S.-W. (1988), Halogenation of Resorcinol Derivatives, Bull Korean Chem Soc 9(1):13-15.

In an embodiment, hierridin C is later purified using standard chromatographic and crystallization methods.

In an embodiment, hierridin B and hierridin C were tested for in vitro activity towards the P. falciparum strains, in particular P. falciparum 3D7 strain and the multidrug-resistant Dd2 strain to verify whether the chlorine atom featured in hierridin C affects the activity of the compound, in particular the antimalarial activity. Furthermore, the results for hierridin B and hierridin C were compared (table 1).

In an embodiment, the laboratory-adapted P. falciparum 3D7 and Dd2 strains were cultivated on human erythrocytes suspended in RPMI 1640 medium supplemented with 25 mM HEPES, 6.8 mM hypoxanthine and 10% AlbuMAX II (Life Technologies, Carlsbad, Calif., USA), at pH 7.2. Cultures were maintained at 37° C. under an atmosphere of 5% O$_2$, 3-5% CO$_2$ and N$_2$, and synchronized by sorbitol treatment prior to the assays. Staging and parasitaemia were determined by light microscopy of Giemsa-stained thin blood smears.

In an embodiment, the antimalarial activities of hierridin B and hierridin C were determined using the SYBR Green I (Life Technologies). Early ring stage parasites were tested in triplicate in a 96-well plate and incubated with drugs for 48 h (37° C., 5% CO$_2$), parasite growth was assessed with SYBR Green I. Each compound was tested in a concentration ranging from 10-0.0097 μM (0.2% DMSO). Fluorescence intensity was measured with a multi-mode microplate reader (Triad, Dynex, Chantilly, Va., USA) with excitation and emission wavelengths of 485 nm and 535 nm, respectively, and analyzed by nonlinear regression using GraphPad Prism 5 (GraphPad Software, La Jolla, Calif., USA). Surprisingly, hierridin C presented a lower $IC_{50}$ value in comparison with the hierridin B, demonstrating that it is necessary to use a lower concentration of hierridin C, than of hierridin B, to obtain 50% of inhibition of *P. falciparum* 3D7.

TABLE 1

$IC_{50}$ values for hierridin B and hierridin C in *P. faldparum* strains

| *P. faldparum* 3D7 $IC_{50}$ (μM) | | *P. faldparum* Dd2 $IC_{50}$ (μM) | |
|---|---|---|---|
| Hierridin B | Hierridin C | Hierridin B | Hierridin C |
| 2.09 ± 0.08 | 1.52 ± 0.05 | 2.25 ± 0.67 | 2.31 ± 0.11 |

Figure 3:
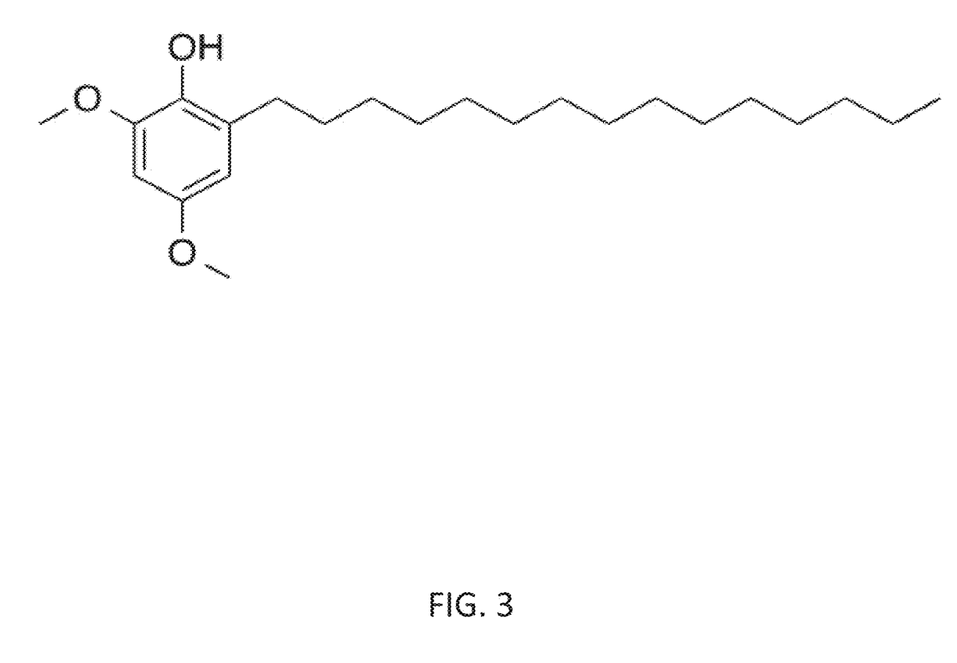
FIG. 3: Chemical structure of hierridin B.

While all $IC_{50}$ values obtained were in the low-micromolar range, hierridin C was more potent than hierridin B against the 3D7 strain. The two metabolites, hierridin B (FIG. 3) and hierridin C (FIG. 4), showed equal potency towards the Dd2 strain.

In an embodiment, the hierridin C showed ~2 μM $IC_{50}$ in *P. falciparum* strains, including mefloquine and chloroquine resistant strain *P. falciparum* Dd2. This results in a >=50 therapeutical index.

In an embodiment, several cell lines were exposed to hierridin C, in particular to a concentration of hierridin C up to 30 μg mL$^{-1}$ (75.2 μM). The cell lines exposed to hierridin C, were in particular the cell lines of hepatocellular carcinoma HepG2, colon adenocarcinoma HT-29, neuroblastoma SH-SY5Y, breast carcinoma T47D, normal prostate cell line PNT2, breast adenocarcinoma, RKO colon carcinoma and MG-63 osteosarcoma. No cytotoxicity was observed in any of the cell lines tested.

All references recited in this document are incorporated herein in their entirety by reference, as if each and every reference had been incorporated by reference individually.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims.

The present disclosure should not be seen in any way restricted to the embodiments described and a person with ordinary skill in the art will foresee many possibilities to modifications thereof.

The above described embodiments are combinable. The following claims further set out particular embodiments of the disclosure.

The invention claimed is:

1. A compound of the following formula or a pharmaceutically acceptable salt, ester, solvate or prodrug thereof,
wherein
R1 is a halogen;
R2, R4 are independently selected from the group consisting of C1-C6 alkyl, H, COCH3, COH, CO-alkyl, and CO-aryl; and
R3 is a C10-C30 alkyl.

2. The compound of claim 1, wherein
R1 is selected from the group consisting of F, Cl, and Br;
R2, R4 are independently selected from a group consisting of C1-C6 alkyl; and
R3 is a C15-C21 alkyl.

3. The compound of claim 1, wherein R2 and R4 are equal.

4. The compound of claim 1, wherein the compound is 3-chloro-4,6-dimethoxy-2-pentadecylphenol.

5. A pharmaceutical composition comprising:
a compound as defined in claim 1 in a therapeutically effective amount; and
a pharmaceutically acceptable excipient.

6. The pharmaceutical composition of claim 5, wherein the pharmaceutically acceptable excipient is a carrier, adjuvant, excipient or a mixture thereof.

7. The pharmaceutical composition of claim 5, wherein the composition is suitable for topical, oral, parental, or injectable administration.

8. A method for obtaining the compound of 3-chloro-4,6-dimethoxy-2-pentadecylphenol comprising: isolating said compound from a solution comprising a cyanobacterium strain with accession number CCAP1436/1.

* * * * *